US009354188B2

(12) United States Patent
Albiez (10) Patent No.: US 9,354,188 B2
(45) Date of Patent: May 31, 2016

(54) PARTICLE BEAM DEVICE AND METHOD FOR OPERATING A PARTICLE BEAM DEVICE (71) Applicant: Carl Zeiss Microscopy GmbH, Jena (DE)

(72) Inventor: Michael Albiez, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/019,887

(22) Filed: Sep. 6, 2013

(65) Prior Publication Data

US 2014/0070097 A1  Mar. 13, 2014

(30) Foreign Application Priority Data

Sep. 7, 2012  (DE) .......................... 10 2012 215 945

(51) Int. Cl.
*G01N 23/225* (2006.01)
*H01J 37/10* (2006.01)
*H01J 37/26* (2006.01)
*H01J 37/28* (2006.01)

(52) U.S. Cl.
CPC .............. *G01N 23/225* (2013.01); *H01J 37/10* (2013.01); *H01J 37/265* (2013.01); *H01J 37/28* (2013.01); *H01J 2237/0475* (2013.01); *H01J 2237/2449* (2013.01); *H01J 2237/24475* (2013.01); *H01J 2237/2538* (2013.01)

(58) Field of Classification Search
CPC ...... G01N 23/225; H01J 37/10; H01J 37/147; H01J 2237/047; H01J 2237/0473; H01J 2237/0475; H01J 2237/0492; H01J 2237/2538

USPC ............................................. 250/306, 396 R
See application file for complete search history.

(56) References Cited

U.S. PATENT DOCUMENTS 6,498,345 B1  12/2002  Weimer et al.
2004/0036031 A1  2/2004  Rose et al.
(Continued)

FOREIGN PATENT DOCUMENTS

DE  198 28 476 A1  12/1999
DE  101 07 910 A1  8/2002
(Continued)

OTHER PUBLICATIONS

DeLong, A., et al., "Low voltage STEM," Proc. of ICEM, 15, Durban 2002, pp. 107f.
(Continued)

*Primary Examiner* — Jack Berman
*Assistant Examiner* — Kevin Chung
(74) *Attorney, Agent, or Firm* — Muirhead and Saturnelli, LLC (57) ABSTRACT A particle beam device, in particular an electron beam device, is provided having a beam generator for generating a primary particle beam, an objective lens for focusing the primary particle beam onto an object, and a detector for detecting particles emitted by the object. The objective lens has at least one magnetic unit, with the magnetic unit generating at least one first crossover and at least one second crossover. The first crossover is arranged in the objective lens or in a region between the objective lens and the object. The second crossover is arranged at the object. The device permits the examination of the object using particles which have a low energy, with good imaging properties. A method for operating the particle beam device is also provided.

15 Claims, 4 Drawing Sheets

(56) References Cited

U.S. PATENT DOCUMENTS

| | | | |
|---|---|---|---|
| 2008/0149831 A1* | 6/2008 | Saito | G01N 23/203 250/310 |
| 2009/0101818 A1 | 4/2009 | Zach | |
| 2010/0059676 A1* | 3/2010 | Shojo et al. | 250/311 |
| 2010/0200748 A1* | 8/2010 | Adamec et al. | 250/307 |
| 2011/0049361 A1 | 3/2011 | Preikszas et al. | |

FOREIGN PATENT DOCUMENTS

| | | |
|---|---|---|
| DE | 10 2007 049 816 B3 | 4/2009 |
| DE | 10 2009 028 013 A1 | 3/2011 |

OTHER PUBLICATIONS

Hawkes, P. W., "Magnetic Electron Lenses," Practical Lens Design, 1982.

Herrmann, K.H., "The present state of instrumentation in high-resolution electron microscopy," J. Phys. E: Sci. Instrum., vol. 11, 1978, 18 pp.

Boyes, E.D., "Low Voltage Scanning Electron Microscopy," Final Report, Oct. 1988, United States Army, European Research Office of the U.S. Army, Contract No. DAJA 37-82-C-0271, 72 pp.

Rieck, W.D., "Practical lens design," In: *Magnetic Electron Lenses*, ed. By P. W. Hawkes, Springer, 1982, ISBN 3-540-10296-5, preface, table of contents, pp. 180-185.

\* cited by examiner

PARTICLE BEAM DEVICE AND METHOD FOR OPERATING A PARTICLE BEAM DEVICE

TECHNICAL FIELD

This application relates to a particle beam device, in particular an electron beam device, having a beam generator for generating a primary particle beam, having an objective lens for focusing the primary particle beam onto an object plane (or onto an object) and having a detector for detecting particles emitted by the object plane (or by the object). This application furthermore relates to a method for operating the particle beam device.

BACKGROUND OF THE INVENTION

Electron beam devices, in particular scanning electron microscopes are used, for example to examine surfaces of objects (specimens). In a scanning electron microscope, a primary electron beam having electrons is to this end generated using the beam generator. The primary electron beam is focused onto the object to be examined by an objective lens. It is also known to guide the primary electron beam in a raster-scan pattern over the surface of the object to be examined using a deflection device. In the process, the electrons of the primary electron beam interact with the object. As a result of the interaction, in particular electrons are emitted from the object (what is referred to as secondary electrons), or electrons of the primary electron beam are scattered back (what is referred to as back-scattered electrons). The back-scattered electrons here generally have an energy in the range of 50 eV up to the energy of the electrons of the primary electron beam at the object. The secondary electrons furthermore generally have an energy of less than 50 eV. The secondary electrons and/or back-scattered electrons are detected using at least one detector. The detector is arranged for example inside the objective lens or in a region between the objective lens and the beam generator. When the secondary electrons and/or the back-scattered electrons impinge on the detector, a detector signal is generated which is used to generate an image.

Imaging of an object using an electron beam device can be achieved with high spatial resolution. The high spatial resolution is obtained owing to the primary electron beam having a very low diameter in the plane of the object. Furthermore, the spatial resolution is the better, the closer the object is arranged to the objective lens of the electron beam device. Furthermore, the spatial resolution is the better, the greater the electrons of the primary electron beam in the electron beam device are initially accelerated and decelerated to a desired energy (examination energy) at the end in the objective lens or in the region between the objective lens and the object. The electrons of the primary electron beam are accelerated, for example, with an acceleration voltage of 2 kV to 30 kV and guided through an electron column of the electron beam device. The electrons of the primary electron beam are decelerated to the desired energy only in the region between the objective lens and the object, such that the electrons of the primary electron beam have, for example, an energy in the range of 10 eV to 30 keV, with which they impinge on the object.

There are objects, which, owing to their structure, can be examined in an electron beam device in a meaningful manner only if the electrons of the primary electron beam impinging on said objects have only a low energy, for example an energy of less than 100 eV. Electrons having such a low energy ensure that said particular objects are not destroyed when being irradiated by electrons. Electrons with such low energies are furthermore particularly suitable for generating an image of an object to be examined having a high surface sensitivity (that is to say with particularly good information content as regards the surface of the object). Moreover, electrons with such low energies are suitable for positioning measurements devices with pointy ends (what is referred to as a prober) at an object, in which electrical measurements are carried out using said prober. Electrons with higher energies than the above-mentioned low energies can possibly falsify such electrical measurements. Therefore, the use of electrons of the primary electron beam, which have such a low energy, are useful for investigating said objects.

However, it has been found that secondary electrons, which owing to the impingement of electrons of the primary electron beam are emitted by the object with an energy of less than 100 eV, are deflected into the electron column due to the acceleration voltage used for the primary electron beam and the field pattern or due to an existing magnetic field and/or electric fields for the electrons of the primary electron beam. Accordingly, a large portion of said secondary electrons can be used for imaging only if they are detected with a detector that is arranged in the electron column.

Such a detector is known from the prior art. Said known detector is constructed to be annular and has a relatively large opening. The optical axis of the electron beam device extends through the opening. The opening is necessary so as not to influence the primary electron beam in the beam path of the electron beam device and to avoid possible contamination.

Reference is made by way of example to DE 198 284 76 A1 and DE 10 2009 028 013 A1 as regards the prior art, which are incorporated herein by reference.

However, it has been found in examinations using electrons of the primary electron beam which have a low energy (for example less than 100 eV) that, owing to the field pattern already mentioned above, the paths of most secondary electrons travel very closely to the optical axis of the electron beam device, with the energies of the secondary electrons and of the electrons of the primary electron beam deviating only slightly from one another. Since the secondary electrons therefore have almost the same energy as the electrons of the primary electron beam, the secondary electrons travel on similar paths through the electron beam device as the electrons of the primary electron beam. Secondary electrons, which emanate from places of the object which, when scanning the object to be examined, are somewhat remote from the optical axis of the electron beam device, also travel in the electron beam device and in particular in the plane of the detector outside the optical axis. They are detected at least partially by the detector in the electron beam device. However, a large portion of the secondary electrons which emanate from places of the object close to the optical axis pass through the opening of the detector without being detected by the detector. Secondary electrons which emanate from places that are remote from the optical axis, by contrast, are incident on the detector. An image of the object to be examined is obtained, wherein the image practically has a detection hole in the middle, since no electrons are detected at this place and thus no image information is available.

Another problem is furthermore known from the prior art. It has been shown that, in the case of relatively small working distances of approximately 1 mm to 2 mm, the mentioned problem is very pronounced. An examination using electrons of the primary electron beam having an energy of less than 1 keV (for example 100 eV) is not possible or possible only with great difficulty in the case of short working distances using the known electron beam devices.

Moreover, it has been shown that an examination of an object using electrons of the primary electron beam having an energy of less than 100 eV is also dependent on the beam generator used. Not every beam generator allows such an examination. For example it is known to use a Schottky emitter for generating the primary electron beam. In a Schottky emitter, electrons are extracted from the Schottky emitter due to an extractor voltage of an extractor electrode. The extractor voltage is typically between 3 kV and 5 kV. Considerations have concluded that the acceleration voltage with which the primary electron beam is guided through the electron column of the electron beam device should be greater than the extractor voltage. However, the higher the selected acceleration voltage, the fewer secondary electrons impinge on the detector if the electrons of the primary electron beam have an energy of less than 100 eV when impinging on the object. The higher the acceleration voltage, the smaller the relative energy difference between the electrons of the primary electron beam and the secondary electrons. It follows that the secondary electrons basically travel along the same optical path as the electrons of the primary electron beam and therefore pass through the opening of the detector. The abovementioned problem of the detection hole is very pronounced in the case of high acceleration voltages. Furthermore, the maximum working distance becomes increasingly small. The result in principle is that an image of the object using electrons of the primary electron beam having an energy of less than 100 eV is almost not possible at an acceleration voltage of greater than 4 kV. However, since the accelerator voltage is supposed to be greater than the extractor voltage of an emitter, this can lead to a problem, because beam generators are known which require an extractor voltage of greater than 4 kV. In that case, however, the accelerator voltage is also greater than 4 kV. As a result, examination of an object using electrons of the primary electron beam having an energy of less than 100 eV is almost impossible.

Accordingly, it would be desirable to specify a particle beam device and a method for operating a particle beam device, with which an object can be examined using particles having a low energy such that in particular good imaging of the object is achieved.

SUMMARY OF THE INVENTION

The particle beam device according to the system described herein has at least one beam generator for generating a primary particle beam. The particle beam device according to the system described herein furthermore has at least one objective lens for focusing the primary particle beam onto an object plane of an object (or onto an object). In addition, the particle beam device according to the system described herein is provided with at least one detector (referred to below as first detector), wherein the first detector serves for detecting particles emitted by the object plane (or by the object).

The objective lens has at least one magnetic unit. The magnetic unit is constructed and excited such that at least two crossovers of the primary particle beam are generated in series one after the other by the objective lens. Provision is made in particular for at least a first crossover and at least a second crossover to be generated. In the above text and also below, a crossover is understood to mean a point or region at which the particles generated by the particle generator converge. In other words, the particles intersect at this point or this region. In yet other words, a crossover is thus understood to mean a region or a plane in which the dimensions of the primary particle beam emanating from the beam generator have a local minimum in directions perpendicular to the propagation direction of the primary particle beam. If the primary particle beam perpendicular to the propagation direction has an approximately Gaussian distribution, a crossover along the propagation direction is a region in which the Gaussian bell curve has the smallest width. The width of the bell curve is thus in each case wider before and after the crossover—as viewed in the beam direction (propagation direction)—than in the crossover. In astigmatic focusing of the primary particle beam, the crossover is typically understood to mean that plane between the two (or between two) line foci in which the primary particle beam has a rotationally symmetrical intensity distribution with minimum dimensions perpendicular to the propagation direction of the primary particle beam.

Additionally or alternatively, an exemplary embodiment of the system described herein provides for the first crossover to be arranged in the objective lens or in a region between the objective lens and the object plane (or the object). It furthermore provides for the second crossover to be arranged at the object plane (or the object). In other words, the second crossover is arranged on the surface of the object or in a region near the surface of the object (for example at a distance of 1 μm to 1000 μm from the surface of the object). In particular, the second crossover can be arranged within the depth-of-field range, which in this type of imaging can be several millimeters. The position of the second crossover in this type of imaging can additionally have a significantly greater working distance in the order of magnitude of up to 20 mm. This will be explained in more detail further below.

The system described herein proceeds from the surprising finding that the magnetic unit of the objective lens can be excited so strongly that not only a single crossover is generated, but a plurality of crossovers are generated, for example the previously mentioned first crossover and the previously mentioned second crossover. The system described herein is based in particular on the finding that it is not the first crossover that is arranged on the object, but the second crossover is arranged on the object. As a result, the particles of the primary particle beam already converge in a crossover (first crossover) before they converge in a further crossover (second crossover) on the surface of the object. It has surprisingly been found that, owing to the previously described manner of operation of the magnetic unit of the objective lens, aberrations are generated which are so strong that the trajectories of the particles emitted by the object clearly differ from the trajectories of the primary particles of the primary particle beam. It has been shown that a significant portion of the secondary particles impinge on the detector, which is arranged, for example, in a particle beam column. It is thus possible to obtain sufficiently good images of the object, in which primary particles with a low energy (for example less than 100 eV) are used for examining the object. The above-described problem of the detection hole is no longer present in the system described herein or present to only a minor degree such that still sufficient image information is available, such that a good image of the object is achievable.

Another advantage of the system described herein is that examinations of the object at a great working distance (for example of up to 10 mm) are now possible even with low energies with which the primary particles impinge on the object. Owing to the greater working distance, numerous examination methods or examination devices can now be used. For example it is possible to arrange a further detector between the objective lens and the object, which detector provides a sufficiently good detection signal. Additionally and/or alternatively, provision may be made for the arrangement of, for example, a gas supply device, a micro-manipulator and/or a prober between the objective lens and the object.

Additionally, the particle beam device according to the system described herein allows an object to be examined at a relatively small working distance of approximately 1 mm to 2 mm, without the above-mentioned problem of the detection hole occurring. Owing to a sufficiently good detection signal, a good signal-to-noise ratio is furthermore achieved, such that the contrast in an image of the object is good.

In an embodiment of the particle beam device according to the system described herein, it is additionally or alternatively possible to switch between a first operating mode of the particle beam device and a second operating mode of the particle beam device. In the first operating mode, a first crossover and a second crossover are generated in the region between the objective lens and the object, with the first crossover being arranged in a region between the objective lens and the object. The second crossover is arranged on the object, as has already been explained further above. In the second operating mode, only a single crossover is generated in the region between the objective lens and the object and arranged on the object. As a result, the particle beam device according to the system described herein has the advantages which are achievable in the two previously mentioned operating modi. In the first operating mode, good detection of interaction particles at a small working distance and the use of a large working distance with low energy of the primary particles of, for example, less than 100 eV are achievable. In the second operating mode, it is possible to achieve a very high resolution of the image of the object generated using the interaction particles.

Due to the at least two crossovers in the region between the objective lens and the object, higher error coefficients occur in the objective lens, which can degrade the resolution of the image of the object generated using the particle beam device. By introducing a corrector in the beam path of the particle beam device between the beam generator and the objective lens for correcting for example the chromatic and spherical aberrations of the objective lens, it is possible for example to correct these chromatic and spherical aberrations and thus to achieve a desired high resolution of the particle beam device. Apparatuses for correcting imaging aberrations are known for example from DE 10 2007 049 816 B3 or DE 101 07 910 A1, which are incorporated herein by reference. The apparatuses described in these publications can be embodied in the particle beam device according to the system described herein.

Another advantage is that, on the basis of the system described herein, acceleration voltages, with which the primary particle beam is guided through the particle beam column of the particle beam device, of greater than 4 kV can easily be realized, specifically independently of the beam generator used.

The particle beam device according to the system described herein also allows the use of any beam generator. This is because the particle beam device according to the system described herein ensures that the above-mentioned problem of the detection hole no longer occurs, independently of the operating voltage of the beam generator.

An exemplary embodiment of the particle beam device according to the system described herein additionally or alternatively makes provision for the particle beam device to have at least one condenser unit (for example a first condenser unit) for shaping the primary particle beam. The first condenser unit is arranged for example between the beam generator and the objective lens. Moreover, a further exemplary embodiment additionally or alternatively provides for a further condenser unit (for example a second condenser unit) to be arranged for shaping the primary particle beam in the particle beam device. Said second condenser unit is arranged, for example, between the beam generator and the objective lens. When using two condenser units, provision is in particular made first for the first condenser unit, then the second condenser unit, and then the objective lens to be arranged along an optical axis of the particle beam device from the beam generator, as viewed in the direction of the object. Both the objective lens with its magnetic unit and the first condenser unit and/or the second condenser unit serves/serve for shaping the primary particle beam on the object.

In yet another exemplary embodiment of the particle beam device according to the system described herein, provision is additionally or alternatively made for the objective lens to have at least one electrostatic unit. The latter contributes, together with the magnetic unit, to the focusing of the primary particle beam or focuses the primary particle beam onto the object.

In yet another exemplary embodiment of the particle beam device according to the system described herein, provision is additionally or alternatively made for the particle beam device to have at least one particle energy control unit for accelerating particles of the primary particle beam to a first prespecified energy and for maintaining the prespecified energy after the acceleration. Provision is made for example for guiding the particles of the primary particle beam with the first prespecified energy through a beam column of the particle beam device. Only just before the particles of the primary particle beam reach the object, they are decelerated by the particle energy control unit to a second prespecified energy, for example by an electrostatic unit, which can also have a focusing action. Said particles are subsequently guided onto the object. Owing to the pre-described function and action of the particle energy control unit, a high luminance of the primary particle beam is maintained even for particles of the primary particle beam, the second prespecified energy of which is under 100 eV, because the deceleration of the primary particle beam to the second prespecified energy is carried out only just before the object is reached. The deceleration to the second prespecified energy occurs here in the objective lens or in a region between the objective lens and the object.

An embodiment of the particle beam device according to the system described herein additionally or alternatively provides for the first detector to be arranged in the beam column of the particle beam device. In an exemplary embodiment of the particle beam device according to the system described herein, provision is furthermore additionally or alternatively made for the particle beam device to have at least a second detector for detecting particles that are scattered back at the object, for example back-scattered electrons. Said second detector is likewise arranged, for example, in the beam column.

In yet another exemplary embodiment of the particle beam device according to the system described herein, provision is additionally or alternatively made for the particle beam device to be constructed as an electron beam device. The electron beam device is constructed for example as a scanning electron microscope. The beam generator in that case serves for generating a primary electron beam having electrons. The objective lens serves for focusing the primary electron beam onto the object plane (or onto the object). The first detector for example serves for detecting electrons (secondary electrons) that are emitted by the object plane (or by the object).

Provision is alternatively made for the particle beam device to be constructed as an ion beam device. In this case, the beam generator is constructed for generating a primary ion beam having ions. Furthermore, the objective lens is constructed for focusing the primary ion beam onto the object plane (or onto the object). The first detector serves for detecting particles, for example electrons, emitted by the object plane (or by the object).

The system described herein also relates to a method for operating a particle beam device, for example a particle beam device having at least one of the above-mentioned features or a combination of at least two of the above-mentioned features. For example, the particle beam device has at least one beam generator for generating a primary particle beam, and at least one objective lens for focusing the primary particle beam. Provision is made in the method according to the system described herein for the objective lens to be excited such that it generates at least two crossovers in series one after the other in the propagation direction of the primary particle beam, for example a first crossover and a second crossover.

In an exemplary embodiment of the method according to the system described herein, additionally or alternatively, for generating an image of a surface of an object interaction particles, which are generated owing to an interaction between the primary particle beam and the object, are detected using at least one detector which is arranged between the beam generator and the objective lens. By way of example, the interaction particles are secondary particles (in particular secondary electrons) and/or particles that are scattered back at the object (in particular back-scattered electrons).

In a further exemplary embodiment of the method according to the system described herein, provision is additionally or alternatively made for primary particles of the primary particle beam to have an energy of less than 1 keV when impinging on the object plane (or the object). The primary particles of the primary particle beam have, for example, an energy of less than 100 eV when impinging on the object plane (or on the object).

BRIEF DESCRIPTION OF THE DRAWINGS

Embodiments of the system described herein will be explained in more detail below with reference to the figures which are briefly described as follows.

DETAILED DESCRIPTION OF VARIOUS EMBODIMENTS

The system described herein will be explained in more detail using a particle beam device in the form of a scanning electron microscope (SEM). However, it is expressly noted that the system described herein is not limited to an SEM. Rather, the system described herein can be realized in any particle beam device, in particular in an ion beam device or in particular in a field ion microscope.

Figure 1:
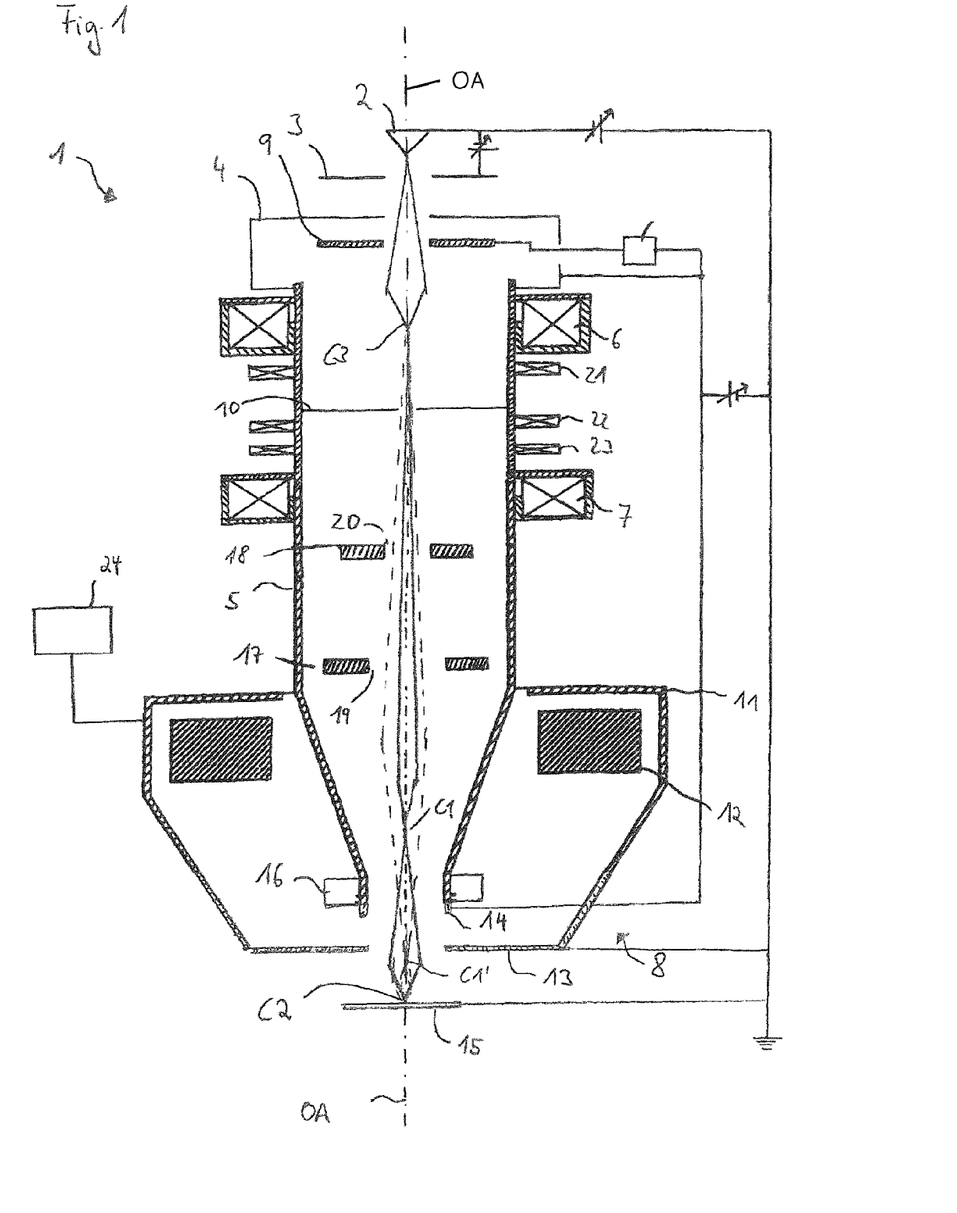
FIG. 1 shows a first exemplary embodiment of a scanning electron microscope.

FIG. 1 shows a schematic illustration of a first exemplary embodiment of an SEM 1. The SEM 1 has a beam generator in the form of an electron source 2 (cathode), an extraction electrode 3 and an anode 4, which is placed onto one end of a beam guiding tube 5 of the SEM 1. The electron source 2 is constructed for example as a thermal field emitter. However, the system described herein is not limited to such an electron source. Rather, any electron source can be used.

Electrons emerging from the electron source 2 form a primary electron beam. The electrons are accelerated to anode potential owing to a potential difference between the electron source 2 and the anode 4. The anode potential in the exemplary embodiment illustrated here is 1 kV to 20 kV with respect to a ground potential of a housing of a specimen chamber (not illustrated), for example 5 kV to 15 kV, in particular 8 kV, alternatively it could also be at ground potential.

Two condenser lenses are arranged on the beam guiding tube 5, specifically a first condenser lens 6 and a second condenser lens 7. Starting from the electron source 2 in the direction of an objective lens 8, first the first condenser lens 6 and then the second condenser lens 7 are arranged.

A first aperture unit 9 is arranged between the anode 4 and the first condenser lens 6. The first aperture unit 9, together with the anode 4 and the beam guiding tube 5, is at high-voltage potential, specifically the potential of the anode 4 or alternatively at ground. Arranged between the first condenser lens 6 and the second condenser lens 7 is a spatially fixed second aperture unit 10.

The objective lens 8 has objective lens pole pieces 11, in which a hole is formed. The beam guiding tube 5 is guided through said hole. Furthermore, a coil 12 is arranged in the pole pieces 11. The objective lens pole pieces 11 and the coil 12 form a magnetic unit of the objective lens 8.

An electrostatic delay device is connected downstream of the beam guiding tube 5. Said delay device has an individual electrode 13 and a tube electrode 14, which is formed at the end of the beam guiding tube 5 that faces a specimen 15. The individual electrode 13 is, in the illustrated embodiment, electrically insulated with respect to the objective lens pole pieces 11 and furthermore mechanically connected to the objective lens pole pieces 11. In another embodiment, provision is alternatively made for the individual electrode 13 to be arranged inside the objective lens pole pieces 11, but in a first region which extends from the tube electrode 14, as viewed in the direction of the specimen 15. Alternative provision is made for the individual electrode 13 to be arranged in a second region, with the second region extending from the objective lens pole pieces 11, as viewed in the direction of the specimen 15, and with the second region extending from the specimen 15, as viewed in the direction of the electron source 2. This means that the individual electrode 13 can be arranged at any desired position in a region between the tube electrode 14 and the specimen 15.

The tube electrode 14, together with the beam guiding tube 5, is thus at the potential of the anode 4, while the individual electrode 13 and specimen 15 are at a potential that is lower with respect to the potential of the anode 4. In the present case, this is the ground potential of the housing of the specimen chamber (not illustrated). In this manner, the electrons of the primary electron beam can be decelerated to a desired energy that is necessary for the examination of the specimen 15. By way of example, the electrons of the primary electron beam are decelerated to an energy below 1 keV, in particular below 100 eV. This energy is also referred to as examination energy or landing energy.

The SEM 1 furthermore has a scanning unit 16, by way of which the primary electron beam can be deflected and scanned over the specimen 15. The electrons of the primary electron beam here interact with the specimen 15. As a result of the interaction, interaction particles and/or interaction radiation is/are generated which is/are detected. The detection signals obtained in this manner are evaluated.

The interaction particles are in particular electrons emitted from the surface of the specimen 15 (what is referred to as secondary electrons), or are electrons of the primary electron beam that are back-scattered (what are referred to as back-scattered electrons). For the detection of secondary electrons and/or the back-scattered electrons, a detector arrangement is arranged in the beam guiding tube 5, having a first detector 17 and a second detector 18. The first detector 17 is in this case arranged on the side of the specimen along the optical axis OA, while the second detector 18 is arranged on the source-side along the optical axis OA in the beam guiding tube 5. Furthermore, the first detector 17 and the second detector 18 are arranged mutually spaced apart in the direction of the optical axis OA of the SEM 1. Both the first detector 17 and the second detector 18 are approximately at the potential of the anode 4 and thus also at the potential of the beam guiding tube 5.

The first detector 17 has a first through-opening 19. Furthermore, the second detector 18 has a second through-opening 20. The optical axis OA of the SEM 1 extends both through the first through-opening 19 and through the second through-opening 20. The primary electron beam consequently travels through the second through-opening 20 and through the first through-opening 19, and is subsequently guided to the specimen 15. The first through-opening 19 of the first detector 17 and the second through-opening 20 of the second detector 18 have their longest extents in the range of 0.5 mm to 5 mm. They are for example circular in construction and have a diameter in the range of 0.5 mm to 3 mm.

The first aperture unit 9 in the exemplary embodiment illustrated here is in the form of a pinhole aperture and has an opening for the through-passage of the primary electron beam, which opening has an extent in the range of 10 µm to 500 µm, for example 50 µm.

The second aperture unit 10 is, in the exemplary embodiment illustrated here, constructed as a pinhole aperture and has an opening for the through-passage of the primary electron beam, which opening has an extent in the range of 5 µm to 300 µm, for example 35 µm. The second aperture unit 10 is constructed as a pressure stage aperture. It separates a first region, in which the electron source 2 is arranged and in which an ultra-high vacuum prevails ($10^{-6}$ to $10^{-10}$ Pa), from a second region, which has a high vacuum ($10^{-1}$ to $10^{-5}$ Pa). The second region is the intermediate pressure region of the beam guiding tube 5, which guides to the specimen chamber (not illustrated). With the second aperture unit 10, the deterioration of the ultra-high vacuum of the first region owing to contamination from the second region, for example owing to the introduction of gases in the region of the specimen 15, is avoided.

In order to additionally influence the beam profile of the primary electron beam, a first deflection unit 21, a second deflection unit 22 and a third deflection unit 23 are arranged on the beam guiding tube 5.

The magnetic unit of the objective lens 8 is connected to a control unit 24, which then controls the magnetic unit such that the magnetic unit of the objective lens 8 generates a first crossover C1 and a second crossover C2. In the exemplary embodiment discussed here, additionally the focusing action of the electrostatic delay device is used. Explicit mention is made of the fact that the generating of the first crossover C1 and of the second crossover C2 can also be effected exclusively by the magnetic unit of the objective lens 8. In the SEM 1, it is certainly possible for more crossovers to be present in the beam path along the optical axis OA, for example a third crossover C3 in the region between the anode 4 and the second aperture unit 10. What is crucial, however, is that the magnetic unit of the objective lens 8 generates at least two crossovers. Reference is made to the statements already made above. In the exemplary embodiment illustrated here, these are the first crossover C1 and the second crossover C2.

The first crossover C1 is arranged in the objective lens 8. Alternatively, provision is made for the first crossover to be arranged in a region between the objective lens 8 and the specimen 15 (dashed lines of the beam profile; the first crossover is designated with the reference sign C1'). The second crossover C2 is arranged at the specimen 15. In other words, the second crossover C2 is arranged on the surface of the specimen 15. In yet other words, the specimen 15 is positioned such that the optical axis OA intersects the surface of the specimen 15 at a location that is located inside the depth-of-field range of the second crossover C2.

The first detector 17 serves for the detection of electrons at a low energy, for example in a range between 0 eV and 50 eV. These are primarily secondary electrons. The electrons of the primary electron beam which are decelerated to the landing energy generate these secondary electrons, which emerge from the specimen 15 and are directed through the objective lens 8. Owing to the strong excitation of the objective lens 8 and the formation of the first crossover C1 and of the second crossover C2, said secondary electrons are deflected in a large solid angle. This deflection occurs surprisingly, although the energy of the secondary electrons in the beam guiding tube 5 deviates only slightly from the energy of the electrons of the primary electron beam guided through the beam guiding tube 5.

By contrast, only a very small portion of electrons which are scattered back at the specimen 15 (back-scattered electrons), which have a high kinetic energy when emerging from the specimen 15 as compared to the secondary electrons and thus have an energy in the beam guiding tube 5 that is even closer to the energy of the electrons of the primary electron beam guided through the beam guiding tube 5, are captured by the first detector 17, since said back-scattered electrons are focused relatively closely to the optical axis OA by the objective lens 8 (thus like the electrons of the primary electron beam) and can thus pass through the first through-opening 19 of the first detector 17. However, the back-scattered electrons are captured by the second detector 18. The detection signals generated with the first detector 17 and the second detector 18 are used to generate an image or a plurality of images of the surface of the specimen 15.

Figure 2:
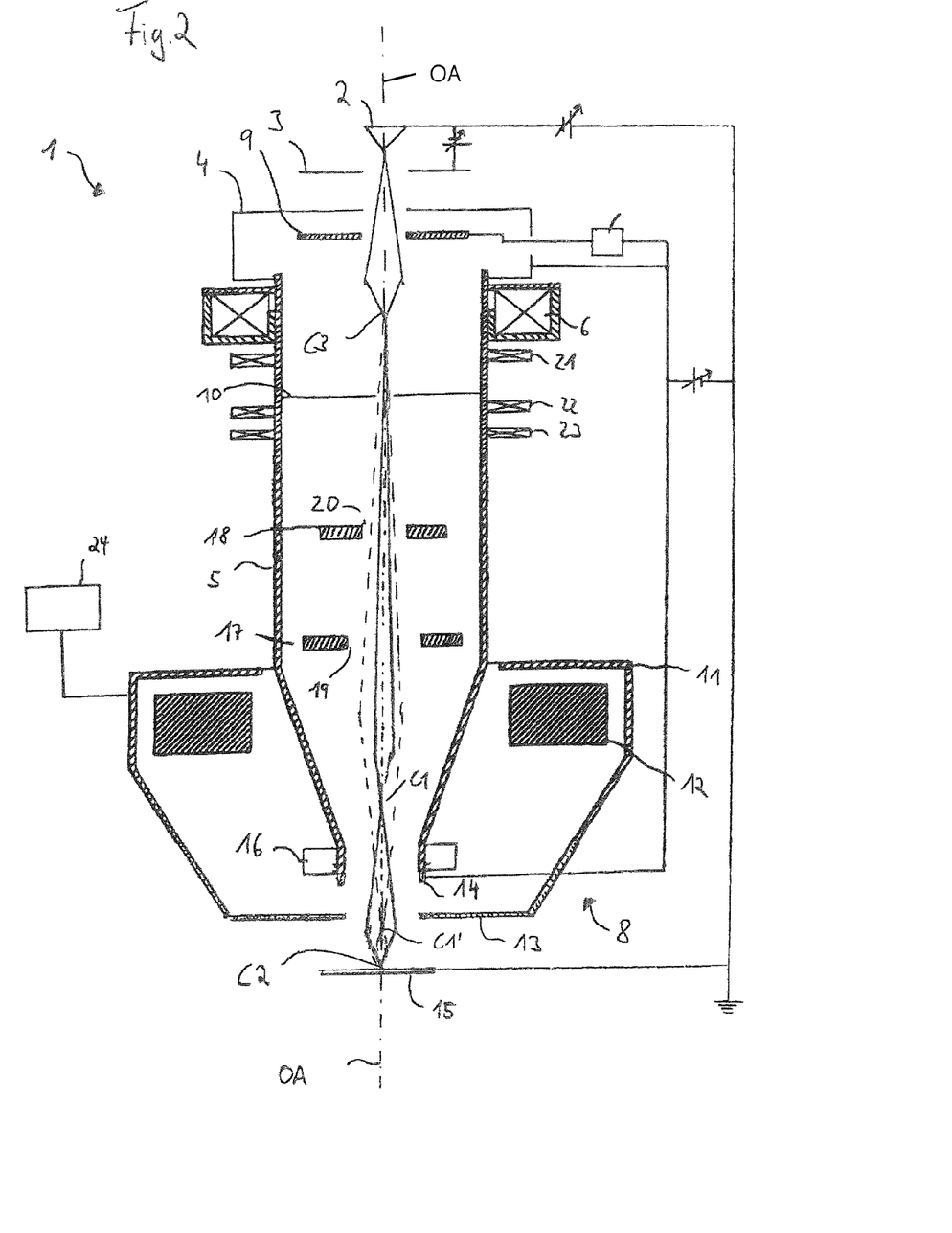
FIG. 2 shows a second exemplary embodiment of a scanning electron microscope.

FIG. 2 shows a schematic illustration of a second exemplary embodiment of the SEM 1. The exemplary embodiment in FIG. 2 is based on the exemplary embodiment in FIG. 1. Identical components are therefore designated with the same reference signs. In contrast to the exemplary embodiment according to FIG. 1, the exemplary embodiment in FIG. 2 has only a single condenser unit, specifically the condenser lens 6.

Figure 3:
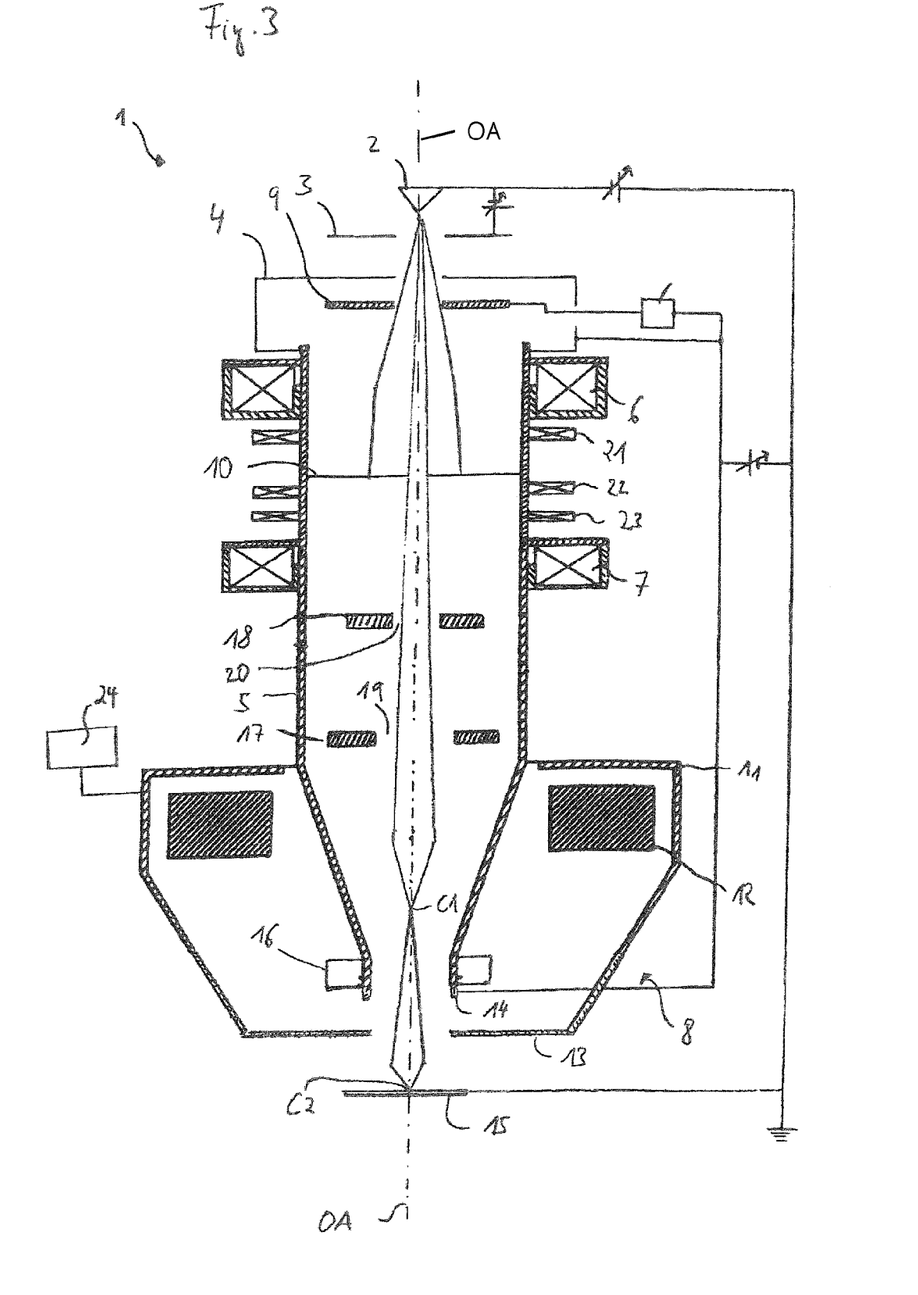
FIG. 3 shows a third exemplary embodiment of a scanning electron microscope.

FIG. 3 shows a schematic illustration of a third exemplary embodiment of the SEM 1. The exemplary embodiment in FIG. 3 is based on the exemplary embodiment in FIG. 1. Identical components are therefore designated with the same reference signs. In contrast to the exemplary embodiment according to FIG. 1, no other crossovers, aside from the first crossover C1 and the second crossover C2, are provided in the beam path of the SEM 1 downstream of the electron source 2 in the direction of the specimen 15.

Figure 4:
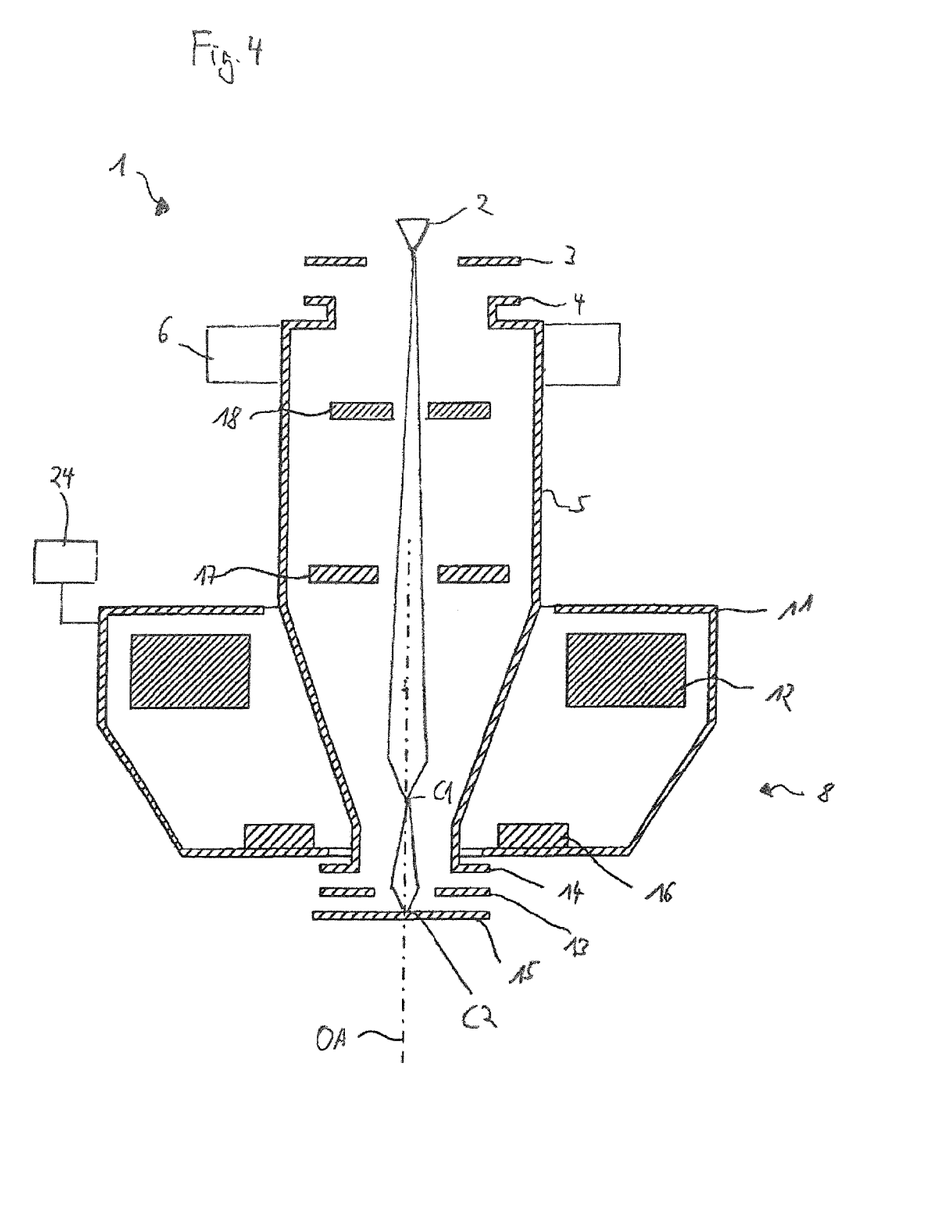
FIG. 4 shows a fourth exemplary embodiment of a scanning electron microscope.

FIG. 4 shows a further exemplary embodiment of an SEM 1. The exemplary embodiment in FIG. 4 is basically based on the exemplary embodiment in FIG. 2. Identical components are designated with the same reference signs. In contrast to the exemplary embodiment in FIG. 2, the individual electrode 13 is arranged in a region between the tube electrode 14 and the specimen 15. Furthermore, in the exemplary embodiment of the SEM 1 illustrated in FIG. 4, only two crossovers are provided in the beam path of the SEM 1 from the electron source 2, as viewed in the direction of the specimen 15, specifically the first crossover C1 and the second crossover C2.

Explicit mention is made of the fact that, in all embodiments, certainly a plurality of crossovers can be present in the beam path of the SEM 1. However, what is crucial is that always two crossovers, that is to say the first crossover C1 and the second crossover C2, are generated by the magnetic unit.

In all exemplary embodiments, the magnetic unit of the objective lens 8 is strongly excited such that a plurality of crossovers are generated, specifically the first crossover C1 or C1' and the second crossover C2. In the exemplary embodiments discussed here, additionally the focusing action of the electrostatic delay device can be used (see above). The electrons of the primary electron beam already converge in the first crossover C1 or C1', before they converge in the second crossover C2 on the surface of the specimen 15. Owing to the previously described mode of operation of the magnetic unit of the objective lens 8 (and, in the exemplary embodiment discussed here, also owing to the focusing action of the electrostatic delay device), such strong aberrations are generated that the trajectories of the secondary electrons emitted by the specimen 15 are considerably different from the trajectories of the electrons of the primary electron beam. A significant portion of the secondary electrons impinge on the first detector 17.

If the aberrations generated by the objective lens 8 should prevent a sufficiently fine focusing of the primary electron beam in the second crossover C2, a corrector can be arranged between the electron source 2 and the two detectors 17 and 18, through which corrector the aberrations generated by the objective lens 8 are countered by a different sign, such that the aberrations generated by the corrector and the aberrations generated by the objective lens 8 completely or at least partially compensate for one another. Corresponding correctors are known in terms of their construction from DE 10 2007 049 816 B3 or from DE 101 07 910 A1, which are incorporated herein by reference. Since, for the secondary electrons emerging from the specimen 15 and/or for the primary electrons scattered back at the specimen 15 (back-scattered electrons), the compensation of the aberrations generated by the objective lens 8 occurs only downstream of the two detectors 17, 18, the paths of the secondary electrons and/or of the back-scattered electrons before reaching the two detectors 17, 18 are off-axis to the same extent as without corrector, such that the compensation of the aberrations owing to the corrector does not disadvantageously affect the detectability of the secondary electrons and/or of the back-scattered electrons.

It is thus possible to obtain sufficiently good images of the specimen 15, in which electrons of the primary electron beam with a low energy (for example less than 100 eV) are used for examining the specimen 15. The problem of the detection hole described above is no longer present or only present to such a small degree that still a sufficient number of electrons, in particular secondary electrons, reach the first detector 17 and thus sufficient image information is available for achieving a good image of the specimen 15.

Additionally, the SEM 1 permits the specimen 15 to be examined with a relatively small working distance of approximately 1 mm to 2 mm, without the above-described problem of the detection hole occurring. The contrast of the image of the specimen 15 is hereby further improved. It also becomes possible to use different beam generators, without the above described problem of the detection hole occurring.

With reference to the figures, the system described herein is explained using exemplary embodiments, in which the objective lens 8 has a superposed magnetic and electrostatic lens. The system described herein is, however, also realizable with a purely magnetic objective lens which generates only one magnetic field for focusing the particle beam. Since the magnetic field extends along the optical axis over a finite distance, even in the case of a purely magnetic lens with a sufficiently great magnetic field strength, it is possible to form two crossovers in series one after the other along the optical axis, in particular if the particle energy of the primary particle beam at this location is less than 1 keV.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with other computers and/or with a user. Software implementations of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for operating a particle beam device having a beam generator that generates a primary particle beam, an objective lens, with a magnetic unit, that focuses the primary particle beam onto an object plane, and a first detector that detects particles emitted by the object plane, the method comprising:
    exciting the objective lens to generate a first crossover and a second crossover in series one after the other in a propagation direction of the primary particle beam; and
    generating aberrations with the objective lens that cause trajectories of particles emitted by the object plane to significantly differ from trajectories of primary particles of the primary particle beam.

2. The method according to claim 1, further comprising:
    detecting interaction particles using the first detector, which is arranged between the beam generator and the objective lens, wherein the interaction particles are generated according to an interaction between the primary particle beam and the object; and generating an image of a surface of an object.

3. The method according to claim 2, wherein the interaction particles that are detected are secondary particles and/or particles that are scattered back at the object.

4. The method according to claim 1, wherein particles of the primary particle beam have an energy of less than 1 keV when impinging on an object.

5. The method according to claim 1, wherein particles of the primary particle beam have an energy of less than 100 eV when impinging on an object.

6. The method according to claim 1, wherein the first detector is arranged in at least one beam column.

7. The method according to claim 1, wherein the first detector has a through opening and wherein an optical axis of the particle beam device extends through the through opening.

8. The method according to claim 1, further comprising:
deflecting particles emitted by an object with the objective lens, and
detecting particles emitted by the object using the first detector.

9. The method according to claim 1, wherein the first crossover is arranged in the objective lens or in a region between the objective lens and the object plane, and wherein the second crossover is arranged at the object plane.

10. The method according to claim 1, further comprising:
shaping the primary particle beam using at least one condenser unit.

11. The method according to claim 1, further comprising:
shaping the primary particle beam using at least two condenser units.

12. The method according to claim 1, further comprising:
accelerating particles of the primary particle beam to a first prespecified energy using a particle energy control unit;
maintaining the first prespecified energy after the acceleration; and
decelerating the particles of the primary particle beam to a second prespecified energy.

13. The method according to claim 1, further comprising:
detecting particles that are scattered back at the object plane using a second detector.

14. The method according to claim 1, wherein the particle beam device is an electron beam device and wherein the method further comprises:
generating a primary electron beam using the beam generator;
focusing the primary electron beam using the objective lens; and
detecting electrons that are emitted by the object plane using the first detector.

15. The method according to claim 1, wherein the particle beam device is an ion beam device and wherein the method further comprises:
generating a primary ion beam using the beam generator;
focusing the primary ion beam using the objective lens; and
detecting electrons that are emitted by the object plane using the first detector.

* * * * *